United States Patent [19]
Bartee et al.

[11] Patent Number: 5,957,690
[45] Date of Patent: Sep. 28, 1999

[54] TEXTURED HIGH DENSITY PTFE MEDICAL BARRIER

[76] Inventors: Barry K. Bartee; Chad M. Bartee, both of 3234 64th St., Lubbock, Tex. 79413

[21] Appl. No.: 08/971,390

[22] Filed: Nov. 17, 1997

[51] Int. Cl.⁶ .............................. A61L 27/00; A61F 2/28
[52] U.S. Cl. ................. 433/215; 623/16; 128/DIG. 14
[58] Field of Search ............................... 433/215, 229, 433/167, 173; 623/16; 128/DIG. 14

[56] References Cited

U.S. PATENT DOCUMENTS

| | | | |
|---|---|---|---|
| 4,187,390 | 2/1980 | Gore | 174/102 R |
| 4,531,916 | 7/1985 | Scantlebury et al. | 433/173 |
| 4,819,478 | 4/1989 | Melcher | 73/61.1 C |
| 4,849,285 | 7/1989 | Dillon | 428/330 |
| 4,859,383 | 8/1989 | Dillon | 264/43 |
| 5,032,445 | 7/1991 | Scantlebury et al. | 428/158 |
| 5,093,179 | 3/1992 | Scantlebury et al. | 428/158 |
| 5,171,148 | 12/1992 | Wasserman et al. | 433/215 |
| 5,196,016 | 3/1993 | Buser et al. | 606/72 |
| 5,197,882 | 3/1993 | Jernberg | 433/215 |
| 5,356,429 | 10/1994 | Seare | 623/8 |
| 5,360,341 | 11/1994 | Abramowitz | 433/215 |
| 5,378,152 | 1/1995 | Elia | 433/215 |
| 5,443,483 | 8/1995 | Kirsch | 606/74 |
| 5,480,711 | 1/1996 | Ruefer | 428/315.5 |
| 5,511,565 | 4/1996 | Syers | 433/229 |
| 5,545,226 | 8/1996 | Wingo et al. | 623/16 |
| 5,607,689 | 3/1997 | Checchi | 433/175 |
| 5,700,479 | 12/1997 | Lundgren | 623/11 |

FOREIGN PATENT DOCUMENTS

| | | | |
|---|---|---|---|
| 574091 | 12/1993 | European Pat. Off. | 433/215 |
| 95/09583 | 4/1995 | WIPO . | |

OTHER PUBLICATIONS

Thomas G. Wilson, Jr., D.D.S., P.C. and Daniel Buser, D.D.S., P.D., Advances in the Use of Guided Tissue Regeneration for Localized Ridge Augumentation in Combination with Dental Implants, Texas Dental Journal 5, Jul. 7–10, 1994.

D. Buser, U. Brägger, N.P. Lang and S. Nyman, Regeneration and Enlargement of Jaw Bone Using Guided Tissue Regeneration Clin. Oral Impl. Res. 1990: 1: 22–32.

Todd V. Scantlebury, 1982–1992: A Decade of Technology Development for Guided Tissue Regeneration, J. Periodontol 1993; 64:1129–1137.

*Primary Examiner*—Ralph A. Lewis
*Attorney, Agent, or Firm*—Thomas and Knight, P.C.; Raymond M. Galasso; Jonathan E. Jobe

[57] ABSTRACT

A medical barrier that includes a sheet of unsintered substantially unexpanded polytetraflouroethylene (PTFE) polymer material having a density in a range of about 1.2 gm/cc to about 2.3 gm/cc, and preferably in the range of about 1.45 gm/cc to about 1.55 gm/cc, and having at least one textured surface. Preferably, the sheet has one textured surface and one substantially smooth surface, and has substantially uniform strength in all directions.

3 Claims, 2 Drawing Sheets

TEXTURED HIGH DENSITY PTFE MEDICAL BARRIER

FIELD OF THE INVENTION

The present invention relates generally to implantable medical products and more particularly to a textured high density polytetrafluoroethylene (PTFE) medical barrier for use in guided tissue regeneration in the repair of bone defects, and particularly in the repair of alveolar bone defects.

DESCRIPTION OF THE PRIOR ART

Regeneration of bone defects remains a significant clinical problem in oral reconstructive surgery. Bone defects may occur as a result of tooth extraction, cyst formation, surgery, trauma, or destruction by periodontal or peri-implant disease. Several synthetic membrane materials have been used for guided tissue regeneration, including cellulose acetate filter, perforated Teflon® mantle leaf, expanded polytetrafluoroethylene (PTFE), and resorbable polymers. Naturally derived membranes such as bovine collagen and lyophilized dura mater have also been used.

Membrane-assisted guided tissue regeneration techniques are based on the hypothesis that during wound healing, cells adjacent to the bone defect migrate to repopulate the defect at various rates. By placing a barrier such as a biocompatible membrane over the defect, the rapidly migrating connective tissue cells will be mechanically prevented from entering the defect. Theoretically, this allows the slower-migrating mesenchymal cells from the surrounding bone and marrow, having osteogenic potential, to repopulate the defect selectively.

A common feature of earlier synthetic membrane systems is macroporosity, which was believed to enhance regeneration by improving wound stability through tissue integration and allowing diffusion of extra-cellular nutrients across the membrane. However, the use of macroporous biomaterials in the oral cavity may result in early bacterial contamination of the material. Bacterial contamination of macroporous biomaterials may result in antibiotic-resistant infection, which can require early removal of the device.

Additionally, a common feature of macroporous biomaterials is the ingrowth of surrounding tissues, which was thought to be necessary for stabilization of the implant. In macro porous biomaterials, cells readily incorporate into the material and connective tissue is manufactured. While this incorporation into the material slows the migration of cells, it presents a difficult problem to the patient and the surgeon during the removal process. The incorporated cells and fibrous connective material may make removal of the barrier painful and traumatic to the patient and very time consuming and difficult for the surgeon.

Recently, it has been discovered that the use of a flexible high-density polytetrafluoroethylene (PTFE) sheet material is useful in guided tissue regeneration. High density PTFE is substantially nonporous or microporous so as not to incorporate cells or attach to fibrous adhesions. By presenting a smooth surface to the biological materials, a high density PTFE barrier is easily inserted and removed following extended implantation periods. An example of a high density PTFE barrier material is disclosed in U.S. Pat. No. 5,480,711.

While high density PTFE medical barriers provide advantages over macroporous barriers, the smooth surface of the high density PTFE barriers sometimes leads to dehiscence of the soft tissue overlying the barrier. The dehiscence problem is caused by the fact that the smooth surface of high density PTFE will not incorporate cells and will not attach to fibrous adhesions. Thus, over the course of healing, the incision will occasionally split open over the high density PTFE barrier.

SUMMARY OF THE INVENTION

The present invention provides a medical barrier that includes a sheet of unsintered substantially unexpanded polytetrafluoroethylene (PTFE) polymer material having a density in a range of about 1.2 gm/cc to about 2.3 gm/cc, and preferably in the range of about 1.45 gm/cc to about 1.55 gm/cc, and having at least one textured surface. Preferably, the sheet has one textured surface and one substantially smooth surface, and has substantially uniform strength in all directions.

The sheet of medical barrier of the present invention has a thickness in a range of about 0.125 mm to about 0.25 mm. Preferably, the textured surface is formed by a plurality of indentations formed in the surface of the sheet. The indentations have a depth less than the thickness of the sheet and each indentation has a preferred width of about 0.5 mm. The indentations are distributed substantially uniformly over the surface of the sheet. Preferably, the indentations are distributed over the surface of the sheet at about 196 indentations per square centimeter.

The medical barrier of the present invention is particularly well adapted for use in guided tissue regeneration in the repair of bone defects, and particularly in the repair of alveolar bone defects. The barrier prevents the entry of rapidly migrating gingival tissue cells into the defect and allows the alveolar bone to regenerate. During healing, the gingival tissue adheres somewhat to the textured surface of the barrier to anchor the gingival tissue over the barrier, thereby preventing dehiscence or splitting open of the tissue covering the material. However, the high density unexpanded substantially non-porous nature of the medical barrier of the present invention prevents gingival tissue from growing into or through the barrier. Thus, after the bone defect has healed, the barrier may be removed with a minimum of trauma to the gingival tissue.

DESCRIPTION OF THE PREFERRED EMBODIMENT

Figure 1:
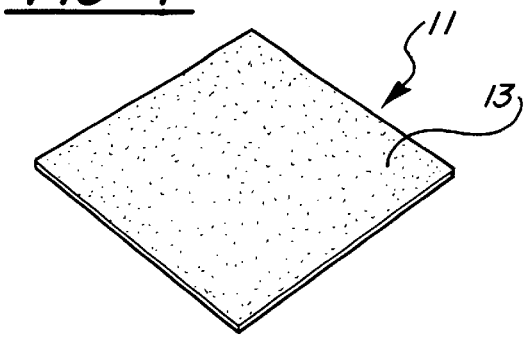
FIG. 1 is a perspective view showing the textured surface of the medical barrier of the present invention.
Figure 2:
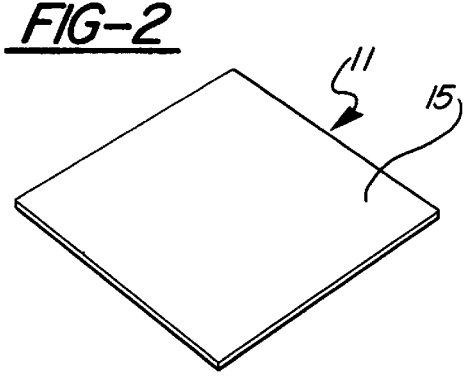
FIG. 2 is a perspective view showing the untextured surface of the medical barrier of the present invention.
Figure 3:
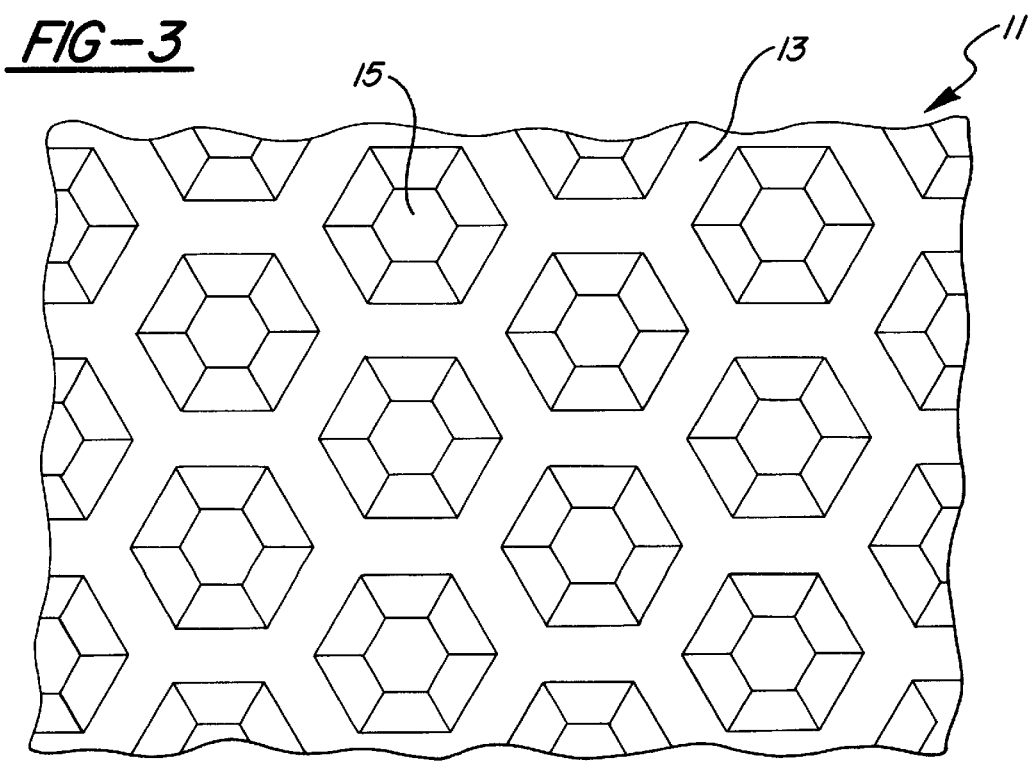
FIG. 3 is an enlarged view of the textured surface of the medical barrier of the present invention.

Referring now to the drawings, and first to FIGS. 1 and 2, a medical barrier according to the preferred embodiment of the present invention is designated generally by the numeral 11. Barrier 11 comprises a sheet of unsintered substantially unexpanded polytetrafluoroethylene (PTFE) polymer. As shown in FIG. 1, barrier 11 includes a textured surface 13, and as shown in FIG. 2, an untextured surface 15. Barrier 11 has a density in the range of about 1.2 gm/cc to about 2.3 gm/cc, and preferably in the range of about 1.45 gm/cc to about 1.55 gm/cc. Barrier 11 has a sheet thickness in the range of about 0.125 mm to about 0.25 mm. As shown in FIG. 3, the textured surface of the preferred embodiment is formed by a plurality of indentations 15 formed in surface 13 of barrier 11. In the preferred embodiment, indentations 15 are hexagonal in shape, although other shapes are within the scope of the present invention. The indentations have a depth less than the thickness of the sheet, and in the preferred embodiment indentations 15 are about 0.15 mm deep. Preferably, indentations 15 are about 0.5 mm wide.

Indentations 15 are distributed substantially uniformly over surface 13 of barrier 11 at about 150 indentations per square centimeter to about 250 indentations per square centimeter. Preferably, indentations 15 are distributed over surface 13 of sheet 11 at about 196 indentations per square centimeter.

The barrier of the present invention is made by first forming a thin sheet of unsintered PTFE and then embossing the sheet with indentations. PTFE resin is mixed with a lubricant such as mineral spirits to form a paste. The paste is then calendered in multiple passes between rollers to form a thin flat sheet of the desired thickness in the range of about 0.125 mm to 0.25 mm. The calendering is performed multiple times in multiple directions to reduce the thickness of the sheet and to impart substantially uniform strength in all directions to the sheet. The lubricant is removed by drying the sheet at temperature somewhat above the boiling point of the mineral spirit lubricant, but well below the sintering temperature of PTFE, which is about 327 degrees C. The foregoing process steps result in a flat sheet of unsintered PTFE about 0.125 to 0.25 mm thick, having a density in the range of about 1.2 gm/cc to about 2.3 gm/cc, and having substantially uniform strength in all directions. The resulting flat sheet has two substantially smooth surfaces.

After the sheet has been dried, the sheet is embossed to form the indentations in one of its surfaces. In the preferred embodiment, the embossing step is performed by placing a sheet of patterned polymer mesh on top of the unembossed sheet of unsintered PTFE. The patterned polymer sheet material, such as polyethylene or polypropylene, that is harder and has more compressive strength than the unsintered PTFE material. The preferred polymer sheet is a fine pore-size sheet filter material manufactured by Tetko, Switzerland. The polymer sheet has a pattern that is embossed into the polymer sheet. The polymer sheet and the unsintered PTFE sheet are passed together between a pair of rollers, which emboss the pattern of the polymer sheet into one surface of the unsintered PTFE sheet. After embossing, the polymer sheet may be discarded. After embossing, the embossed unsintered PTFE sheet may be cut into smaller sheets of various shape and size for packaging and distribution.

Figure 4:
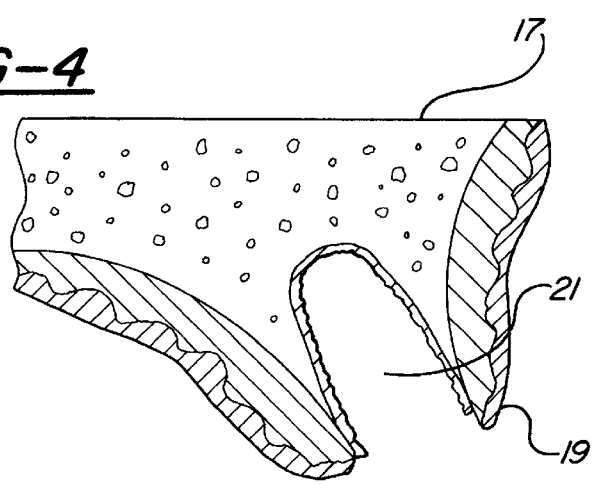
FIG. 4 is a lateral cross-sectional view of a maxillary bony defect resulting from the extraction of a tooth.
Figure 5:
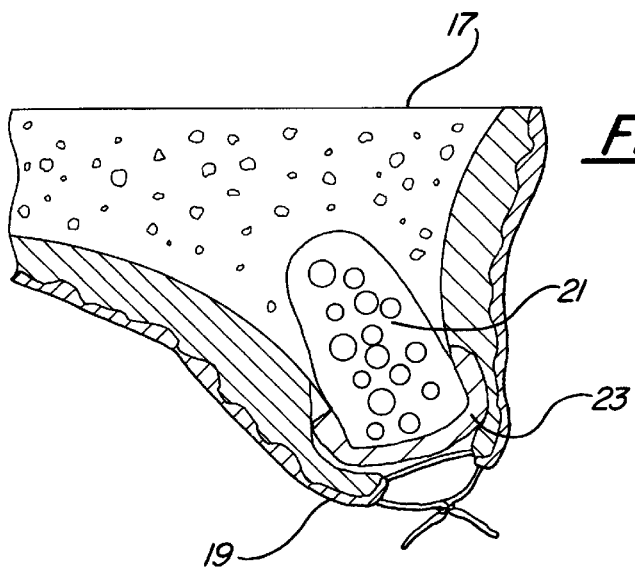
FIG. 5 is a lateral cross-sectional view of the maxillary bony defect of FIG. 4 showing the placement of the medical barrier of the present invention to cover the bony defect with the mucoperiosteal flap sutured over the medical barrier.
Figure 6:
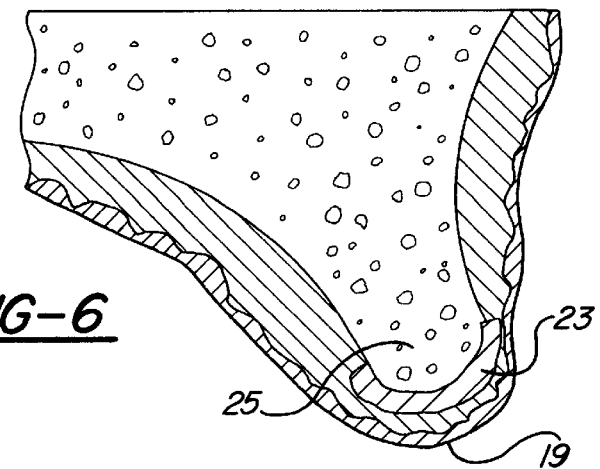
FIG. 6 is a lateral cross-sectional view showing the healed maxillary bony defect of FIGS. 4 with the gingival tissue healed over the medical barrier of the present invention.

Referring now to FIGS. 4–6, there is illustrated the manner of use of the barrier of the present invention. FIG. 4 is a lateral cross-sectional view of an adult human maxilla after a tooth extraction. The bone of the alveolar process is designated by the numeral 17. Soft tissue gingiva 19 covers bone 17. A tooth socket is designate by the numeral 21.

Socket 21 is an example of a bone defect. Other examples of bone defects are those caused by periodontal disease, cyst formation, surgery, or trauma. Normal healing of a defect includes migration of foreign cells such as fibroblasts and gingival epithelial cells. As the cells proliferate into the defect, they inhibit bone cell regeneration, which results in overall loss of bone mass. In the case of extractions, the loss of bone mass results in a loss of alveolar ridge profile.

Referring now to FIG. 5, there is shown one method of using the barrier of the present invention. Socket 19 is shown packed with granular particles of hydroxy apatite as a precursor to bone. Those skilled in the art will recognize that other materials or articles, such as endoceouss-type dental implants, may be placed into socket 21. The packed socket 21 is covered with a layer 23 of the barrier of the present invention. The smooth side of the barrier is placed over socket 21 and bone 17. Thus, the textured of the barrier is positioned adjacent the gingival tissue 19. The substantially uniform strength in all directions of the material of the present invention allows the surgeon to shape layer 23 over socket 21 and bone 17. After layer 23 is placed over socket 21 and bone 17, the gingival flaps 19 are sutured over layer 23. Layer 23 holds the hydroxy apatite particles in place in socket 21 during healing and prevents migration of cells and connective tissue into socket 21. However, connective tissue forms a weak attachment with the textured surface of layer 23, without growing through the material. The attachment is weak enough that the layer may be removed after healing without significant trauma but is strong enough to prevent the dehiscence.

Referring to FIG. 6, there is shown the extraction site after healing, but prior to removal of layer 23. As shown in FIG. 6, the alveolar ridge profile 25 is preserved and the gingival tissue 19 is completely healed over ridge 25. Layer 23 may be removed by making a small incision (not shown) in gingival tissue 19 to expose a portion of layer 23. The layer 23 may then be pulled out with forceps or the like. Since the connective tissue attaches only weakly to the textured surface of the material of the present invention, the material may be pulled out easily and without trauma to the patient.

From the foregoing, it may be seen that the medical barrier of the present invention overcomes the shortcomings of the prior art, and is particularly well adapted for use in guided tissue regeneration in the repair of bone defects, as for example in the repair of alveolar bone defects. The barrier prevents the entry of rapidly migrating gingival tissue cells into the defect and allows the alveolar bone to regenerate. During healing, the gingival tissue adheres somewhat to the textured surface of the barrier to anchor the gingival tissue over the barrier, thereby preventing dehiscence or splitting open of the tissue covering the material. However, the high density unexpanded substantially non-porous nature of the medical barrier of the present invention prevents gingival tissue from growing into or through the barrier. Thus, after the bone defect has healed, the barrier may be removed with a minimum of trauma to the gingival tissue.

What is claimed is:

1. A method of repairing a defect in alveolar bone underlying gingival tissue, which comprises the steps of:

placing a sheet of unsintered substantially unexpanded polytetraflouroethylene polymer material having a density in a range of about 1.2 gm/cc to about 2.3 gm/cc, said sheet having one textured surface and one substantially smooth surface, over said defect between the bone and the gingival tissue with said substantially smooth surface in contact with said bone;

securing the gingival tissue over the sheet;

allowing the defect to heal under the sheet; and, removing the sheet after the defect has healed.

2. A method of preserving alveolar ridge profile following extraction of a tooth, which comprises the steps of:

placing a sheet of unsintered substantially unexpanded polytetraflouroethylene polymer material having a density in a range of about 1.2 gm/cc to about 2.3 gm/cc, said sheet having one textured surface and one substantially smooth surface, over the tooth extraction site between the bone and the gingival tissue surrounding the extraction site with said substantially smooth surface in contact with said bone;

at least partially closing the gingival tissue over the sheet;

allowing the alveolar bone to heal under the sheet; and, removing the sheet after the alveolar bone has healed.

3. The method as claimed in claim 2, including the step of:

filling the extraction site with particulate grafting material prior to placing the sheet.

* * * * *